US010383524B2

(12) United States Patent
Abreu (10) Patent No.: US 10,383,524 B2
(45) Date of Patent: Aug. 20, 2019

(54) SYSTEM FOR CONTROLLING AN ENVIRONMENT OF A STRUCTURE

(71) Applicant: GEELUX HOLDINGS, LTD., Tortola (VG)

(72) Inventor: Marcio Marc Abreu, Bridgeport, CT (US)

(73) Assignee: Geelux Holdings, Ltd., Tortola (VG)

( * ) Notice: Subject to any disclaimer, the term of this patent is extended or adjusted under 35 U.S.C. 154(b) by 203 days.

(21) Appl. No.: 15/332,768

(22) Filed: Oct. 24, 2016

(65) Prior Publication Data

US 2017/0115020 A1 Apr. 27, 2017

Related U.S. Application Data

(60) Provisional application No. 62/245,106, filed on Oct. 22, 2015.

(51) Int. Cl.
| | |
|---|---|
| *A61B 5/00* | (2006.01) |
| *A61B 5/01* | (2006.01) |
| *G05D 23/20* | (2006.01) |
| *G05D 23/19* | (2006.01) |
| *G16H 40/63* | (2018.01) |
| *F24F 11/30* | (2018.01) |
| *A61B 5/11* | (2006.01) |

(Continued)

(52) U.S. Cl.
CPC .............. *A61B 5/01* (2013.01); *A61B 5/0008* (2013.01); *A61B 5/1112* (2013.01); *A61B 5/6803* (2013.01); *A61B 5/6821* (2013.01); *F24F 11/30* (2018.01); *G05D 23/1904* (2013.01); *G05D 23/2033* (2013.01); *G16H 40/63* (2018.01); *F24F 2120/10* (2018.01); *G05B 2219/2614* (2013.01); *G06F 16/29* (2019.01)

(58) Field of Classification Search
CPC ....... A61B 5/01; A61B 5/6803; A61B 5/1112; A61B 5/0008; A61B 5/6821; G05D 23/2033; G05D 23/1904; G16H 40/63; F24F 11/30; F24F 2120/10; G05B 2219/2614; G06F 19/00; G06F 17/30241
USPC ....................................................... 700/278
See application file for complete search history.

(56) References Cited

U.S. PATENT DOCUMENTS 6,640,188 B2 * 10/2003 Hashida ................. G01C 21/28
340/990
2004/0242976 A1 12/2004 Abreu
(Continued)

OTHER PUBLICATIONS

Notification of Transmittal of the International Search Report and the Written Opinion of the International Searching Authority; PCT/US2016/058497 dated Jan. 19, 2017.
(Continued)

*Primary Examiner* — Vu A Vu
(74) *Attorney, Agent, or Firm* — Studebaker & Brackett PC (57) ABSTRACT

A system for modifying controllable elements of a structure based on an array of conditions, particularly a distance of a user or operator from the structure, deviations from an expected travel path to the structure, activities conducted either along or while deviating from the expected travel path, traffic, a core body temperature of the user or operator, and other factors. The controllable structure elements can include, for example, heating and air conditioning (HVAC), alarm, lights, and appliances.

12 Claims, 5 Drawing Sheets

(51) Int. Cl.
  *G06F 16/29* (2019.01)
  *F24F 120/10* (2018.01)

(56) References Cited

U.S. PATENT DOCUMENTS

| | | | | |
|---|---|---|---|---|
| 2009/0105605 A1* | 4/2009 | Abreu | ............... | A61B 5/0008 |
| | | | | 600/549 |
| 2011/0118965 A1* | 5/2011 | Aben | ............... | G01C 21/3476 |
| | | | | 701/117 |
| 2011/0118972 A1* | 5/2011 | Boschker | ........... | G01C 21/3476 |
| | | | | 701/532 |
| 2014/0244156 A1* | 8/2014 | Magnusson | ............ | G01C 21/30 |
| | | | | 701/418 |
| 2014/0309789 A1* | 10/2014 | Ricci | ............... | B60Q 1/00 |
| | | | | 700/276 |
| 2015/0094914 A1 | 4/2015 | Abreu | | |
| 2015/0105687 A1 | 4/2015 | Abreu | | |
| 2015/0196203 A1 | 7/2015 | Abreu | | |
| 2015/0202417 A1 | 7/2015 | Abreu | | |
| 2015/0209174 A1 | 7/2015 | Abreu | | |
| 2015/0312863 A1* | 10/2015 | Shen | ............... | G01S 19/34 |
| | | | | 455/574 |
| 2015/0345960 A1* | 12/2015 | Bennah | ............... | G01C 21/34 |
| | | | | 701/468 |
| 2016/0155342 A1* | 6/2016 | Gibson | ............... | G01S 5/0054 |
| | | | | 701/409 |

OTHER PUBLICATIONS

International Preliminary Report on Patentability issued in Corresponding PCT Application No. PCT/US2016/058497 dated May 3, 2018; 6pp.

\* cited by examiner

SYSTEM FOR CONTROLLING AN ENVIRONMENT OF A STRUCTURE

CROSS-REFERENCE TO RELATED APPLICATIONS

This application claims the benefit of priority to U.S. Provisional Patent Application No. 62/245,106, filed on Oct. 22, 2015, which is hereby incorporated by reference in its entirety.

TECHNICAL FIELD

This disclosure relates to devices configured to control an environment of a structure. Such control considers deviations from typical travel paths between destinations, and activities conducted either along the path of travel or in a deviation from a path of travel. Structure elements can include, for example, heating and air conditioning (HVAC), an alarm, lights, and appliances.

BACKGROUND

Systems exist for automatically modifying air conditioning, heating, and lights based on a distance from home.

SUMMARY

This disclosure provides a system for controlling an environment of a structure, the system comprising at least one temperature sensor, a location device, a mapping system, and a processor. The at least one temperature sensor is sized, dimensioned, and positioned to receive signals from an Abreu brain thermal tunnel (ABTT) terminus of a user and configured to transmit temperature signals representative of the signals received from the ABTT terminus. The location device is configured to determine a location of the user and to transmit signals representative of the location of the user. The mapping system is configured to determine a route of travel of the user and a time to travel the route. The processor is configured to receive the temperature signals from the at least one temperature sensor, the location signals from the location device, and route information from the mapping system, and to control at least one sub-system of the structure based on the temperature of the ABTT when the user reaches a predetermined time from the structure as determined from the route of travel.

This disclosure also provides a system for operating a plurality of devices in a structure, the system comprising a user sub-system and a structure sub-system. The user sub-system includes at least one temperature sensor configured to measure a core body temperature of a user, a device configured to determine a route from a location of the user to the structure, and a transmission device for transmitting information including the core body temperature of the user and the route. The structure sub-system is configured to receive the information transmitted by the user sub-system and operate at least one structure device of the plurality of structure devices based at least in part on the core body temperature of the user, the route of the user, and a calculated predetermined time of arrival of the user at the structure.

This disclosure also provides a method of controlling an environment of a structure, the method comprising receiving a temperature of an ABTT terminus of a user, receiving location information of the user, receiving route information of the user, determining from the route and location information a time of arrival at the structure, and controlling at a predetermined time before arrival of the user at the structure at least one sub-system of the structure based at least in part on the temperature of the ABTT terminus of the user.

Advantages and features of the embodiments of this disclosure will become more apparent from the following detailed description of exemplary embodiments when viewed in conjunction with the accompanying drawings.

DETAILED DESCRIPTION

The present disclosure provides a system for modifying an environment of a structure, such as a building, based on an array of conditions, particularly a distance of a user or operator from the structure and the estimated time to travel that distance, deviations from an expected travel path to the structure, activities conducted either along or while deviating from the expected travel path, traffic, a core body temperature of the user or operator, and other factors. The controllable structure elements can include, for example, heating and air conditioning (HVAC), an alarm, lights, and appliances.

The Abreu brain thermal tunnel (ABTT) provides a unique opportunity to diagnose an array of conditions and diseases that were previously difficult or even impossible to diagnose, and to treat those diseases and conditions, as disclosed by Applicant in co-pending U.S. patent application Ser. No. 14/512,421, filed on Oct. 11, 2014, Ser. No. 14/512,427, filed on Oct. 11, 2014, Ser. No. 14/593,848, filed on Jan. 9, 2015, Ser. No. 14/594,122, filed on Jan. 10, 2015, and Ser. No. 14/603,353, filed on Jan. 22, 2015, incorporated herein by reference in their entirety.

Figure 1:
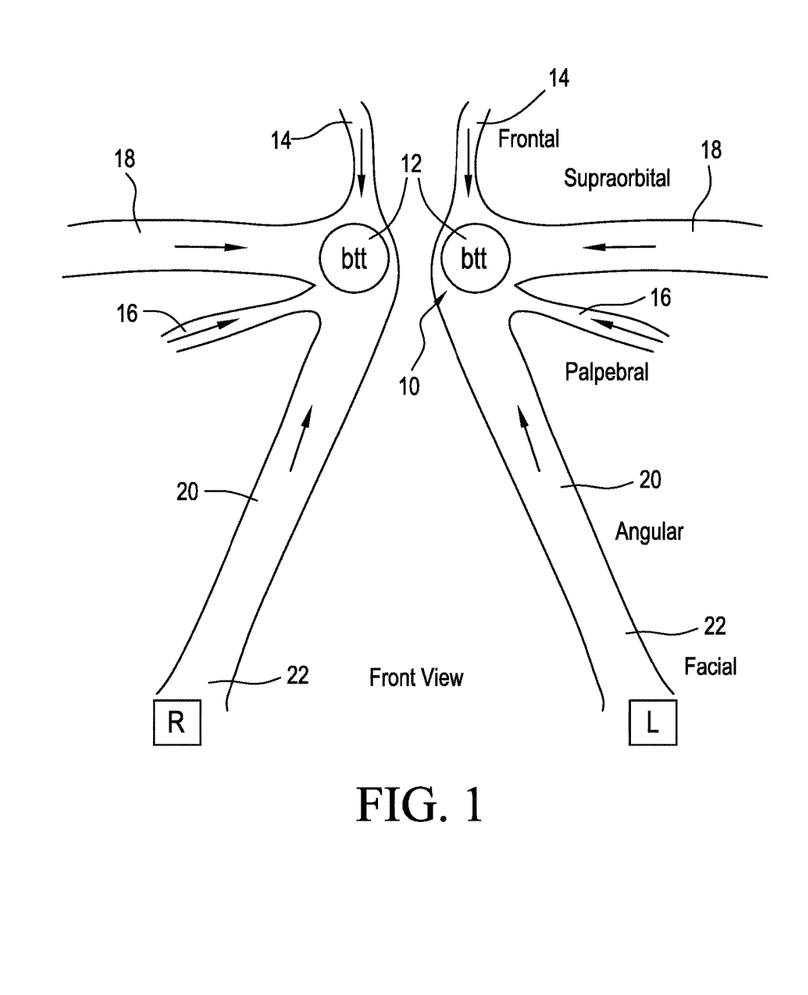
FIG. 1 shows a simplified view of the Abreu brain thermal tunnel (ABTT) and facial veins associated with the ABTT.
Figure 2:
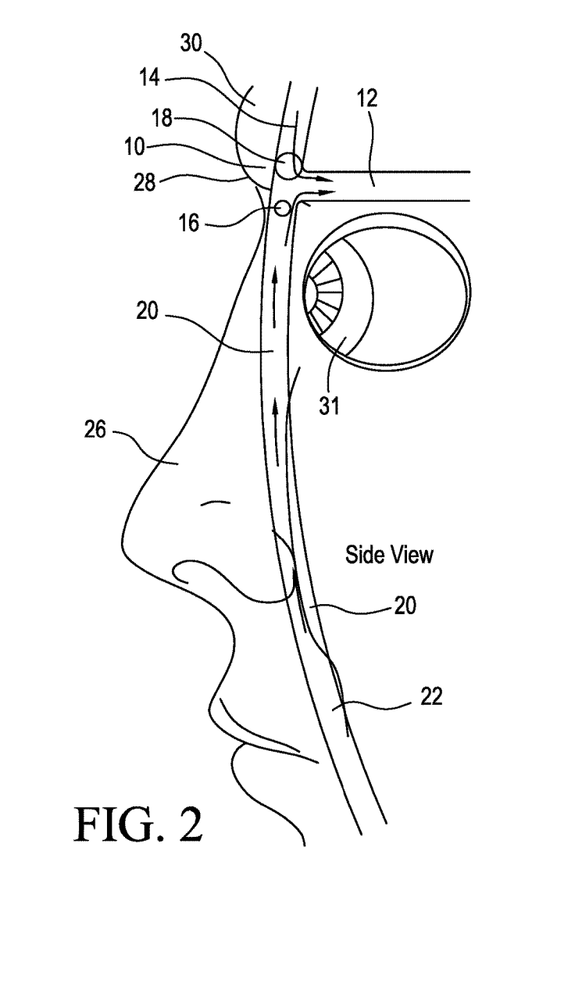
FIG. 2 shows a simplified partial cross-sectional view through a human skull in a vertical direction, showing the ABTT and certain other facial features.
Figure 3:
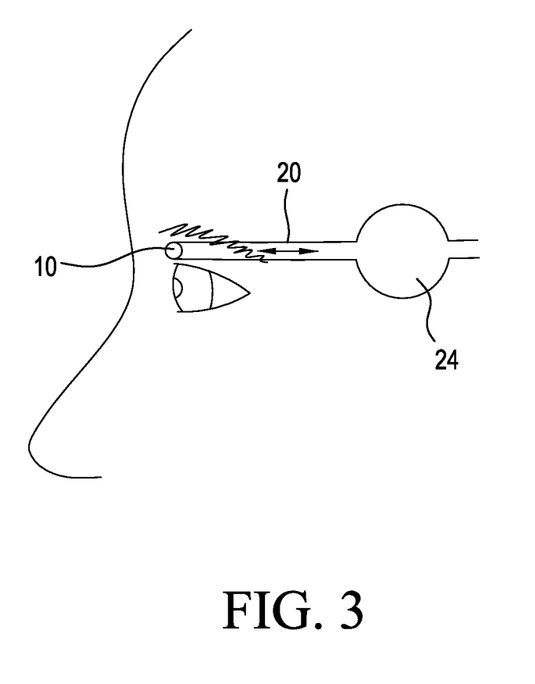
FIG. 3 shows a stylized representation of a flow of blood into a brain core.

The present disclosure arises from the discovery that the Abreu brain thermal tunnel, or ABTT, provides the first known structure for brain-surface thermodynamic communication and thermal connection directly with the center of the brain. Anatomically and physiologically speaking, and as shown in FIGS. 1-3, ABTT 12 includes a continuous, direct, and undisturbed connection between a brain core 24 at the control center of the brain and the skin of ABTT terminus 10. The skin of ABTT terminus 10 is unique in that it is the thinnest skin with the fewest layers of any skin on a human body, it is absent a fat layer, and it has the high thermal conductivity of any skin on the human body.

The physical and physiological events at one end of the tunnel are reproduced at the opposite end. Thus, ABTT 12 enables the direct transfer of temperature signals from brain core 24 to ABTT terminus 10 without significant barriers, as described in co-pending U.S. patent application Ser. No. 14/512,421.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, there is a direct, valve-free connection from ABTT terminus or target area 10 between an eye 32 and an eyebrow 28 into the center of the brain, i.e., brain core 24, which is the temperature center present in the hypothalamus and a thermal storage area present in the cavernous sinus.

FIGS. 1 and 2 show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30, all positioned on a head 34. For the purposes of disclosure, terminology referring to relevant facial areas or veins herein will be described as one or more of the above-referenced veins and ABTT target area 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in pending applications by Applicant, is the thinnest skin in the body and free of fat, providing an unexpectedly rapid communication of temperature from the brain core to the skin of ABTT terminus 10. These vessels lack valves, which are typically an important barrier to blood flow and the direct and rapid transmission of temperature signals. Without valves, these blood vessels truly provide a direct, uninhibited passage for transporting temperature signals directly to and from the hypothalamic region of the brain. Moreover, ABTT 12 includes a superior ophthalmic vein (SOV) 23, which connects the skin surface to the brain and corresponds to the central portion of the tunnel (ABTT 12), is valveless, and has bidirectional blood flow. The SOV lies directly underneath the skin of the superomedial orbit, between eye 32 and eyebrow 28, and is a direct conduit from the surface of the skin at the facial end of ABTT 12, i.e., ABTT terminus 10, to the brain, and then to the hypothalamus. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

The facial end of ABTT 12, herein referred to as a target area, or terminus 10 on the skin on, over, or adjacent to ABTT 12, measures about 11 mm in diameter measured from the medial corner of eye 32 at the medial canthal tendon and extends superiorly for about an additional 6 or 7 mm in an ABTT superior projection (not shown), and then extends into an upper eyelid in a horn-like projection (not shown) for another 22 mm. ABTT terminus 10 is absent fat, and the ABTT superior projection and the horn-like projection are absent fat in areas near to ABTT terminus 10, with a fat layer present in areas a spaced distance away from ABTT terminus 10.

Many aspects of the disclosure are described in terms of sequences of actions to be performed by elements of a computer system or other hardware capable of executing programmed instructions, for example, a general-purpose computer, special purpose computer, workstation, or other programmable data process apparatus. It will be recognized that in each of the embodiments, the various actions could be performed by specialized circuits (e.g., discrete logic gates interconnected to perform a specialized function), by program instructions (software), such as program modules, being executed by one or more processors (e.g., one or more microprocessors, a central processing unit (CPU), and/or application specific integrated circuit), or by a combination of both. For example, embodiments can be implemented in hardware, software, firmware, microcode, or any combination thereof. The instructions can be program code or code segments that perform necessary tasks and can be stored in a non-transitory machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information.

It should be noted that the system of the present disclosure is illustrated and discussed herein as having various modules and units that perform particular functions. It should be understood that these modules and units are merely described based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including, but not limited to, keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

Figure 4:
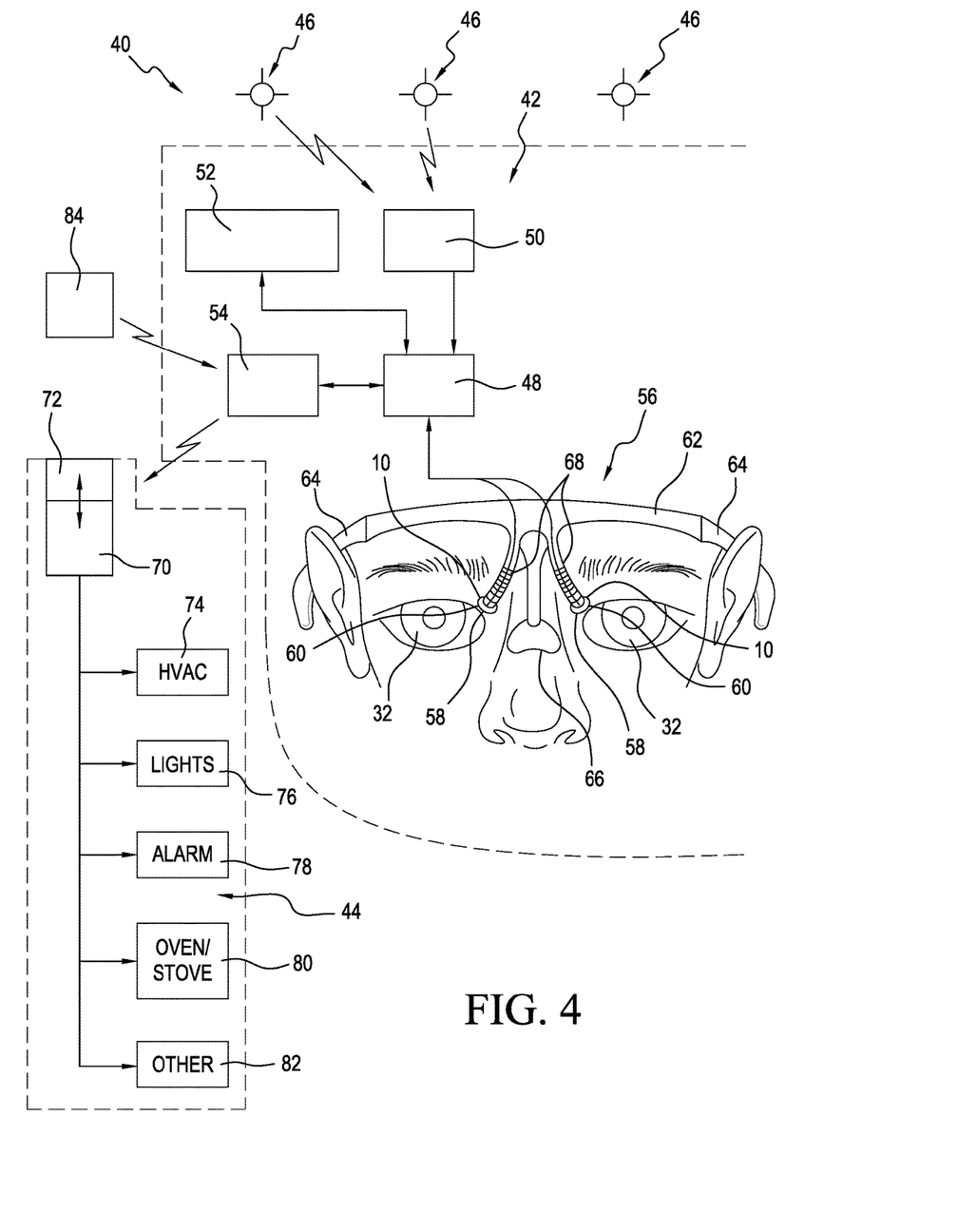
FIG. 4 shows a system in accordance with an exemplary embodiment of the present disclosure.

FIG. 4 shows a structure control system 40 in accordance with an exemplary embodiment of the present disclosure. Structure control system 40 includes a user or operator sub-system (user sub-system) 42 and a structure sub-system 44. Structure control system 40 is configured to receive information from outside sources 84, such as traffic flow, accidents, construction, weather conditions, road conditions, road closures, etc. Structure control system 40 is also configured to receive location information from a location device or system, such as from GPS satellites 46.

The user-subsystem includes a user sub-system processor 48, a GPS receiver 50, a non-transitory memory 52, a transceiver 54, and an ABTT interface 56. Transceiver 54 can be part of a cell phone, a wireless device built into a vehicle, or other system capable of at least transmitting signals wirelessly, and preferably receiving signals wirelessly. The processor can also be included as part of a cell phone, a system built into a vehicle, or other processor. The processor is a physical device, which can be a CPU or can include a CPU, that is connected to various other elements of user sub-system 42 by wire or wirelessly. User sub-system 42 also includes non-transitory memory 52 that serves as a location for the storage of software and data used to perform functions of user sub-system 42.

ABTT interface 56 includes at least a sensor 58 configured to measure the temperature of ABTT terminus 10. Sensor 58 can be a contact sensor that directly measures temperature, an IR sensor, or another device configured to receive thermal signals emitted by or from ABTT terminus 10. If sensor 58 is a contact sensor, it can be positioned in a pad 60 configured to contact ABTT terminus 10. ABTT interface 56 further includes a support frame 62, which can include temple frames 64 and a nose support 66. To position sensor 58 to receive thermal signals optimally from ABTT terminus 10, ABTT interface 56 includes one or more flexible arms 68, and each sensor 58 is positioned at a distal end of flexible arm 68 that is configured to accommodate differences in ABTT location from user to user. A proximate end of flexible arm 68 is attached to support frame 62.

Sensor 58 is configured to transmit signals representative of the temperature or thermal signature of ABTT terminus 10. These signals may be transmitted by wire or wirelessly to user sub-system processor 48, which then uses the data embodied in the signal to perform other functions, described in more detail herein. User sub-system processor 48 is also connected to other elements of user sub-system 42 physically or wirelessly, and transmits or receives signals from these other elements, as appropriate to the element. For example, GPS data from GPS receiver 50 is provided to user sub-system processor 48, data and/or software is transmitted by user sub-system processor 48 to and from non-transitory memory 52, and data and/or control signals are transmitted to transceiver 54. While the exemplary embodiment of FIG. 4 shows that user sub-system processor 48 of user sub-system 42 performs the functions of structure control system 40, a structure processor 70 included as part of structure subsystem 44, described in more detail later, can also perform the functions by receiving information from user sub-system 42 and performing the necessary determinations or calculations.

Structure sub-system 44 includes a structure receiver or transceiver 72, structure processor 70, and a plurality of controllable structure elements or devices, such as HVAC 74, lights 76, alarm 78, appliances 80, and other elements 82. The structure receiver or transceiver 72 is configured to receive signals from transceiver 54 of user sub-system 42. It should be understood that while FIG. 4 shows signals as being transmitted directly from user sub-system 42 to structure sub-system 44, which can be one embodiment of the present disclosure, in other embodiments the signals are transmitted through a cell phone network, via Wi-Fi, or through other transmission systems. Structure processor 70 receives the signals from the structure receiver or transceiver 72, and based on the signals determines whether one or more of the controllable structure elements needs to be operated, such as being turned on, turned off, adjusted, etc.

Figure 5:
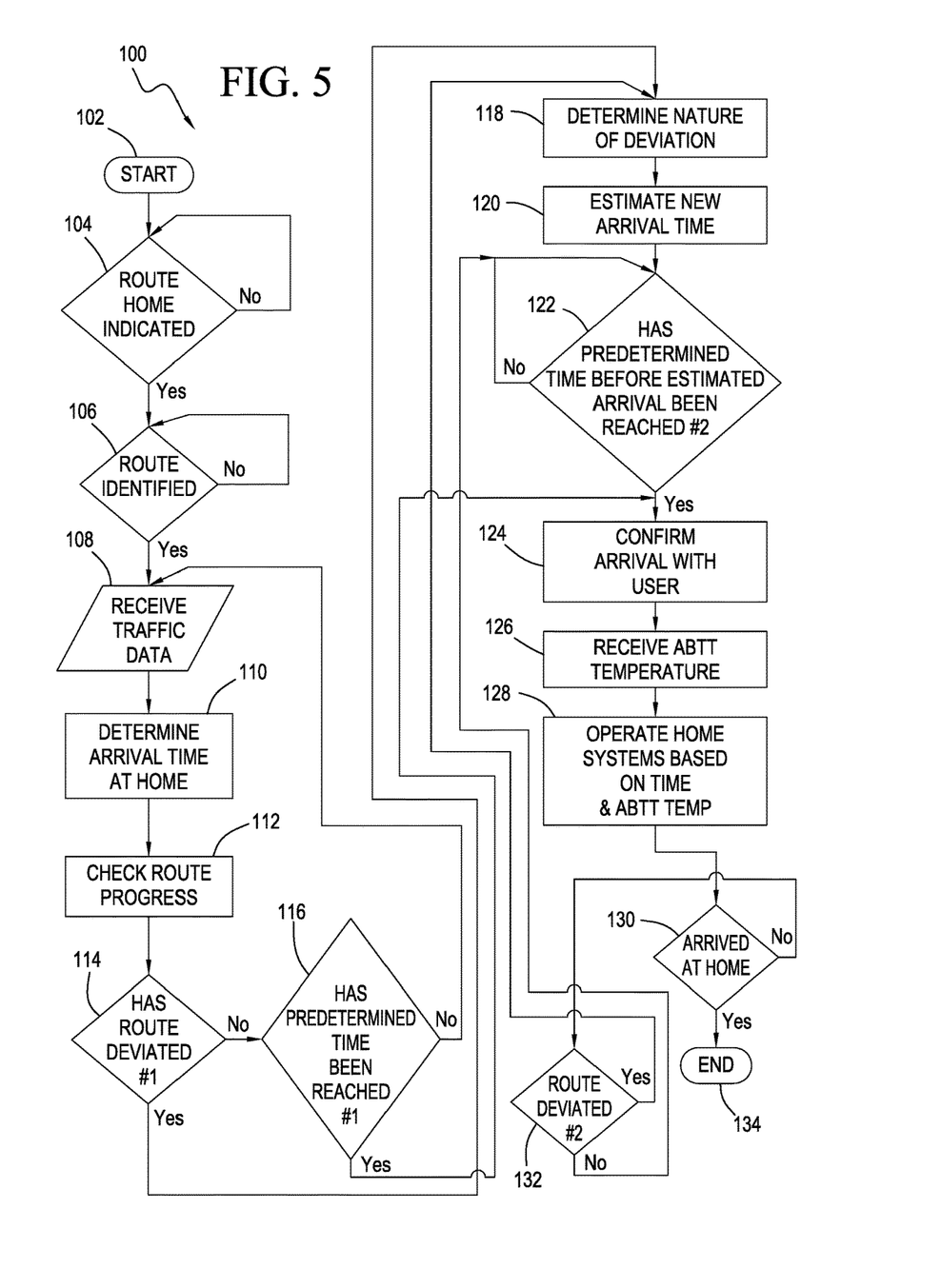
FIG. 5 shows a process flow in accordance with an exemplary embodiment of the present disclosure.
Figure 6:
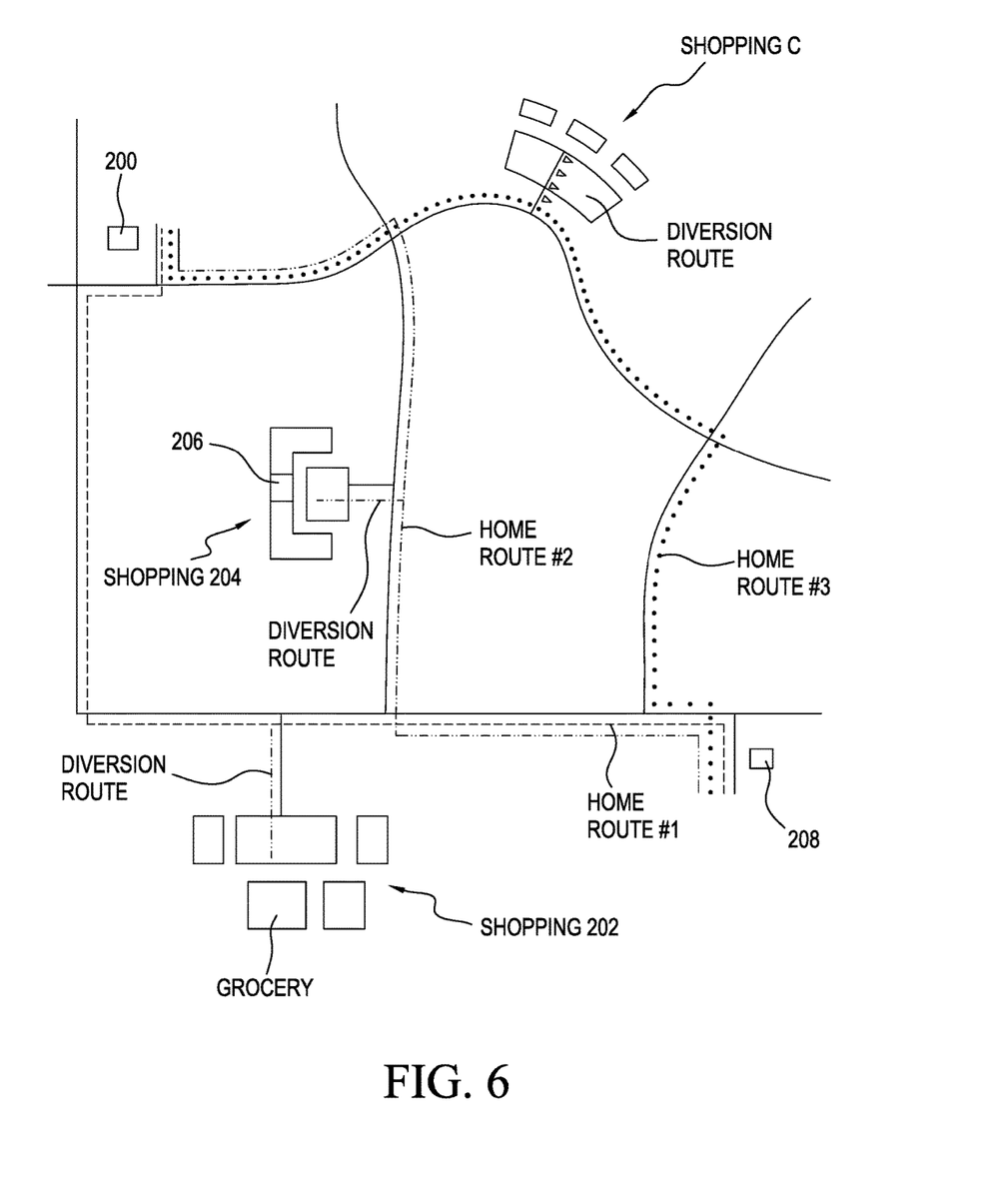
FIG. 6 provides examples of the use of the system and process flow of FIGS. 1 and 2.

FIG. 5 shows an exemplary process flow of structure control system 40, and FIG. 6 shows exemplary examples of the operation of structure control system 40.

As shown in FIG. 5, a structure control system (SCS) process flow begins with a start process 102. Start process 102 is initiated when structure control system 40 is actuated, or, if actuated, start process 102 is initiated when the user is travelling along a route that is typically associated with travel to the structure. Start process 102 can include clearing of registering, loading of software from non-transitory memory 52 to user sub-system 42 processor, etc. Control is then passed from start process 102 to a route to structure decision process 104.

In route to structure decision process 104, wherein an exemplary structure 200 is a house or home 200, a decision is made as to whether a travel route to structure 200 is being taken, such as home route #1, #2, or #3 shown in FIG. 6. Such route information can be made by a mapping device, mapping system, or a processor using map information. If a route home is not detected, control remains with route to structure decision process 104 until a route to home 200 is detected. Once route to structure decision process 104 determines that a route home is detected, control passes from the route to structure decision process 104 to a route identified decision process 106.

In route identified decision process 106, a determination of the route being taken is made. It is typical for more than one route to be available from a first location, such as a work location 208, to a second location, such as home 200. Because the travel time and conditions vary over each route, identification of such routes can be valuable to minimize modifying the environment of structure 200 too early or too late. Early modification wastes energy, and can cause other issues, described in more detail hereinbelow, and late modification can mean less desirable conditions at the destination, such as an overly hot or cold structure, lack of lights, etc. Once a probable route has been determined, control is passed from route identified decision process 106 to a receive data process 108.

In receive data process 108, all available data is received for that route, such as traffic conditions, road conditions, construction, etc., which can be received from, for example, sources 84. It should be understood that while process 108 is shown as a single event, route related data can be continually received throughout process 100 and is used to update process 100 as to when the environment of structure 200 should be controlled. After receipt of data for a particular route, control passes from receive data process 108 to a determine arrival time at home process 110.

At determine arrival time at home process 110, a determination of the approximate arrival time at structure or home 200 is made, based on traffic and other information. Once the approximate arrival time is determined, control is passed from determine arrival time at home process 110 to a check route progress process 112. Control then passes from check route process 112 to a first route deviated decision process 114. In first route deviated decision process 114, a determination is made as to whether a deviation from the identified route exists. If no deviation exists, control passes from first route deviated decision process 114 to a first predetermined time decision process 116. If a route deviation exists, control passes from first route deviated decision process 114 to a determine nature of deviation process 118.

In determine nature of deviation process 118, structure control system 40 uses information from one or more sources to determine how long such deviation is likely to occur. Such information can include, as shown in FIG. 6, that the user has deviated from home route #1 into an area identified as shopping 202. Over time, structure control system 40 can build a history of stops at shopping 202 to estimate how long such a stop is likely to be, incorporating that delay into the calculation for the predetermined time, described further hereinbelow. Such history can be stored in, for example, non-transitory memory 52, and recalled as part of determining or estimating the length of a deviation.

In another example, a deviation can be into an area identified as shopping 204, which includes a fitness center 206. Attendance at fitness center 206 can be recognized by user sub-system 42 because exercise generates measurable thermal signals at ABTT terminus 10. Such measurements can be valuable because structure sub-system 44 can use the thermal signature provided by ABTT terminus 10 to determine actions that need to be taken once the user returns to a route leading to structure 200. For example, if fitness center 206 is approximately 20 minutes from home 200, and the thermal signature at ABTT terminus 10 indicates an elevated core temperature, structure sub-system 44 can compensate for the elevated core temperature by decreasing the temperature of the HVAC system accordingly, meaning by an amount greater than the temperature would otherwise be decreased because the user has been exercising and is hot.

Once the nature of a deviation is determined, control passes from determine nature of deviation process 118 to an estimated arrival time process 120, where a revised arrival time at the structure is determined. In addition, at least one new predetermined time based on the estimated arrival time is determined. The predetermined time is a time at which various controllable structure elements are operated or actuated in advance of the arrival of the user. In an exemplary embodiment, a plurality of predetermined times are determined for each controllable structure element. For example, HVAC system 74 may be operated to reduce structure 200 temperature at a predetermined time of 15 minutes before the estimated arrival time because of the time it takes to heat or cool an enclosed space. Alarm system 78 can be operated to turn off a front door or garage entry at the approximate or estimated arrival time, or a short, predetermined time before the approximate or estimated arrival time. Appliances 80 for cooking, an electric blanket, a whirlpool tub, and other appliances 80 can be operated as selected by the user at predetermined times determined from the estimated arrival time, incorporating core temperature measurements provided by ABTT thermal sensor 58, if appropriate, as described in more detail hereinbelow. For example, the user may prefer to jump into the whirlpool tub within ten minutes of arrival. Process 100 thus controls structure sub-system 44 to automatically fill the whirlpool tub with water of the appropriate temperature at a time that prepares the tub for the arrival of the user, such as five minutes before the estimated time the user typically desires to use the whirlpool tub, with a water temperature that is adjusted based on the thermal signature of ABTT terminus 10. In another example, compact fluorescent lights can be actuated at a predetermined time of 30 seconds before the user's arrival time so that the lights are fully on by the time the user enters structure 200.

Once all predetermined times for various controllable structure elements have been calculated, control passes from estimated arrival time process 120 to a second predetermined time decision process 122. In second predetermined time decision process 122, SCS process flow 100 waits for a first predetermined time to occur, which in an exemplary embodiment is for HVAC 74. At the first predetermined time, control passes from the second predetermined time decision process 122 to a confirm arrival with the user process 124. It should be understood that control can be passed to second predetermined time decision process 122 multiple times. Each time control passes to second predetermined time decision process 122, a determination of a next predetermined time is made. For example, in an exemplary embodiment the total number of systems in a structure to be operated bases on predetermined times can be five, with operation at exemplary times before arrival of 15 minutes, 10 minutes, 7 minutes, 5 minutes and 30 seconds. Once the first predetermined time has passed, the first controllable structure element, for example, HVAC 74, will be operated or actuated. Once the second predetermined time has passed, a second controllable structure element, for example, a cooking appliance 80, can be operated or actuated. Other predetermined times and controllable structure elements are actuated or operated as appropriate until all predetermined times have been reached and the associated elements have been actuated, operated, or otherwise controlled.

Confirm arrival with the user process 124 is an optional process that provides an indication to a user that structure control system 40 has calculated an approximate arrival time, and is controlling various controllable structure elements accordingly. The user can confirm the approximate arrival time, or can adjust the approximate arrival time up or down, based on information known only to the user. If the user elects to not confirm the user's arrival time, SCS process flow 100 moves from confirm arrival with the user process 124 to a receive ABTT temperature process 126.

In receive ABTT temperature process 126, the thermal signature of ABTT terminus 10 is measured to determine a core temperature of the user. This temperature is transmitted to user subsystem processor 48 and/or structure processor 70 for modification of various controllable structure elements. Control then passes from receive ABTT temperature process 126 to an operate structure systems process 128.

In operate structure systems process 128, appropriate structure systems are operated with a separate predetermined time for each system, modified as necessary by the ABTT thermal signature. Once the appropriate system is actuated or operated based on the predetermined time and, as appropriate, the ABTT thermal signature, control passes from the operate structure systems process 128 to an arrived at structure decision process 130.

At arrived at structure decision process 130, system 40 determines whether the user has arrived at structure 200. If the user has arrived at structure 200, all predetermined times have passed and all structure elements operable or controllable by structure control system 40 will have been operated, actuated, or otherwise controlled as appropriate to their function. Control then passes from arrived at structure decision process 130 to an end process 134. However, in another exemplary embodiment, the ABTT interface can remain in place and certain structure systems, for example, HVAC 74, can be dynamically adjusted based on the ABTT thermal signature. In another example, as a user's thermal signature indicates sleep, an electronic blanket can be actuated in preparation for the user to go to bed.

If the user has yet to arrive at structure 200, control passes from arrived at structure decision process 130 to a second route deviated decision process 132, which functions in a manner that is similar to first route deviated decision process 114. If the route has deviated, control passes from second route deviated decision process 132 to determine nature of deviation process 188, which functions as previously described.

Though not specifically shown, structure control system 40 continually receives updated traffic and other information at regular intervals, and system 40 uses the updated traffic and other information to recalculate the estimate arrival time along with all associated predetermined times. One benefit to system 40 of FIG. 4 and process flow 100 of FIG. 5 is that system 40 is continuously adaptable to the driving environment, which includes user-initiated route deviations, without any intervention by the user. Furthermore, the user's physical condition is incorporated into decisions made by structure control system 40 and SCS process flow 100. Thus, the disclosure of FIGS. 4 and 5 is exemplary rather than exhaustive.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A system for controlling an environment, the system comprising:
    a structure;
    a plurality of structure sub-systems located at the structure;
    at least one temperature sensor sized, dimensioned, and positioned between an eyebrow and an eye to receive temperature signals from an Abreu brain thermal tunnel (ABTT) terminus of a user; and
    a first transmitter configured to transmit the temperature signals representative of the signals received from the ABTT terminus;
    a location device configured to determine a location of the user;
    a second transmitter configured to transmit signals representative of the location of the user;
    a mapping system configured to determine at least one route of travel of the user from the location to the structure and a time to travel each of the routes;
    a traffic monitoring system generating traffic data;
    a processor configured to receive the temperature signals from the first transmitter, the location signals from the second transmitter, the traffic data from the traffic monitoring system, and data from the mapping system, the processor controlling at least one of the plurality of structure sub-systems of the structure based on the temperature of the ABTT provided by the first transmitter when the user reaches a predetermined time for travel from the location of the user to the structure as determined from the route of travel provided by the mapping system.

2. The system of claim 1, wherein the processor is configured to identify that the user has stopped along a user-initiated route deviation, and to adjust when the at least one sub-system is controlled based on the location of a user.

3. The system of claim 1, wherein the plurality of structure sub-systems include an HVAC system, lights, an alarm system, and an appliance.

4. A system for operating a plurality of devices to control an environment, the system comprising:
    a structure;
    a plurality of structure sub-systems located at the structure,
    at least one temperature sensor measuring a core body temperature of a user, the at least one temperature sensor being configured and sized to fit between an eyebrow and an eye of the user,
    a route calculating device configured to determine a route from a location of the user to the structure,
    a transmission device transmitting information including the core body temperature of the user and the route,
    one of the plurality of structure sub-systems receiving the information transmitted by the transmission device and the route calculating device and operating the one structure sub-system of the plurality of structure sub-systems based on the core body temperature of the user as provided by the transmission device, the route of the user as provided by the route-calculating device, at least one stop at a location initiated by the user, and a calculated predetermined time of arrival of the user at the structure based at least in part on the location of the at least one stop initiated by the user.

5. The system of claim 4, wherein the calculated predetermined time of arrival of the user at the structure is adjusted based on traffic data received from a traffic monitoring system.

6. The system of claim 4, wherein the plurality of structure sub-systems is controlled at a plurality of predetermined times before arrival of the user at the structure.

7. The system of claim 4, wherein the plurality of structure sub-systems includes at least one of an HVAC system, lights, an alarm system, and an appliance.

8. A method of controlling an environment of a structure, the method comprising:
    generating and transmitting a temperature of an ABTT terminus of a user when the user is located remotely from a structure, the temperature of the ABTT terminus being taken between an eyebrow and an eye of the user,
    generating and transmitting location information of the user when the user is located remotely from the structure;
    generating and transmitting route information of the user when the user is located remotely from the structure;
    determining from the route and location information a time of arrival of the user at the structure;
    determining that the user has initiated a deviation in the route or that the user has stopped, and adjusting the time of arrival of the user at the structure based on the deviation in the route or the stop; and
    controlling at a predetermined time before arrival of the user at the structure at least one sub-system of the structure based at least in part on the temperature of the ABTT terminus of the user.

9. The method of claim 8, further comprising receiving traffic data from a traffic monitoring system and modifying the predetermined time when the at least one sub-system is controlled based at least in part on the received traffic data.

10. The method of claim 8, further comprising identifying the deviation in the route or the stop, and adjusting the predetermined time when the at least one sub-system is controlled based at least in part on the deviation in the route or the stop.

11. The method of claim 8, further comprising identifying that the user has deviated from the route and has stopped along the route, and adjusting the predetermined time when the at least one sub-system is controlled based on identification of the deviation and the stop.

12. The method of claim 8, wherein a plurality of structure sub-systems is controlled at a plurality of predetermined times prior to arrival of the user at the structure.

* * * * *